(12) United States Patent
Walter

(10) Patent No.: US 8,272,225 B2
(45) Date of Patent: Sep. 25, 2012

(54) APPARATUS FOR COOLING CASSETTE MAGAZINES CONTAINING TISSUE SAMPLES

(75) Inventor: Roland Walter, Reilingen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 512 days.

(21) Appl. No.: 12/554,697

(22) Filed: Sep. 4, 2009

(65) Prior Publication Data

US 2010/0058777 A1 Mar. 11, 2010

(30) Foreign Application Priority Data

Sep. 9, 2008 (DE) .......................... 10 2008 046 396

(51) Int. Cl.
*F25B 3/08* (2006.01)
*F25D 25/02* (2006.01)
*F25D 25/00* (2006.01)
(52) U.S. Cl. .................. 62/3.6; 62/381; 62/382; 62/465
(58) Field of Classification Search ....................... 62/3.6, 62/63, 62, 381, 3.2
See application file for complete search history.

(56) References Cited

U.S. PATENT DOCUMENTS

| | | | |
|---|---|---|---|
| 5,635,397 A | 6/1997 | Futschik et al. | |
| 6,228,636 B1 | 5/2001 | Yahiro et al. | |
| 6,251,659 B1 | 6/2001 | Fukuzuno et al. | |
| 6,272,767 B1 | 8/2001 | Botruff et al. | |
| 6,677,857 B2 | 1/2004 | Bara et al. | |
| 6,725,674 B1 * | 4/2004 | Kamm et al. | 62/63 |
| 6,763,665 B2 * | 7/2004 | Clark et al. | 62/3.6 |
| 7,231,771 B2 * | 6/2007 | McMurry et al. | 62/3.6 |
| 2003/0085218 A1 | 5/2003 | Kauschke et al. | |
| 2004/0207303 A1 | 10/2004 | Melching et al. | |
| 2004/0212285 A1 | 10/2004 | Melching et al. | |
| 2006/0063122 A1 | 3/2006 | Heeg et al. | |
| 2007/0199334 A1 * | 8/2007 | MacNair | 62/3.6 |
| 2007/0253866 A1 * | 11/2007 | Rousseau | 422/64 |

FOREIGN PATENT DOCUMENTS

| | | |
|---|---|---|
| AT | 003 118 | 10/1999 |
| DE | 200 04 202 | 8/2000 |
| DE | 101 54 663 | 5/2003 |
| DE | 103 04 171 | 8/2004 |
| DE | 10 2004 043 909 | 3/2006 |
| DE | 10 2005 044 242 | 3/2007 |
| DE | 10 2008 046 396 | 3/2010 |
| EP | 0411224 | 2/1991 |
| EP | 1 447 441 | 8/2004 |
| GB | 715283 | 9/1954 |
| GB | 1094455 | 12/1967 |
| GB | 1280 288 | 7/1972 |
| WO | 91/02202 | 2/1991 |
| WO | 02/059251 | 8/2002 |
| WO | 03/008103 | 1/2003 |

\* cited by examiner

*Primary Examiner* — Judy Swann
*Assistant Examiner* — Jon T Schermerhorn
(74) *Attorney, Agent, or Firm* — Schlee IP International, P.C.; Alexander R. Schlee

(57) ABSTRACT

An apparatus for cooling cassette magazines containing tissue samples is described. The apparatus comprises a housing, a cooling device, and a transport apparatus for transporting one or more cassette magazines within the housing. The cassette magazines are introduced into the apparatus via an input chute and can be removed via an output chute.

12 Claims, 2 Drawing Sheets

APPARATUS FOR COOLING CASSETTE MAGAZINES CONTAINING TISSUE SAMPLES

CROSS-REFERENCE TO RELATED APPLICATION

This application claims the priority of the German patent application DE 102008046396.5 having a filing date of Sep. 9, 2008. The entire content of this prior German patent application DE 102008046396.5 is herewith incorporated by reference.

BACKGROUND OF THE INVENTION

The invention relates to an apparatus for cooling cassette magazines containing tissue samples. The apparatus has a housing and a cooling device.

In a laboratory, tissue samples are ordinarily enclosed in cassettes. The cassettes are labeled in such a way that it is easy to recognize at all times which tissue sample is contained in the corresponding cassette. In order for the cassettes, in particular the tissue samples, to be easily locatable, they are ordinarily organized in cassette magazines. The cassette magazines are in turn equipped with a unique code. It is furthermore known to store the cassette magazines according to fixed laboratory rules, so that in accordance with the laboratory rules regarding allocation of the cassettes to the cassette magazines, the individual tissue samples are stored at fixedly predefined locations and are thus locatable at any time.

The tissue samples must often be cooled, for example in order to section the tissue samples into micrometer-thin slices, for example using a microtome. The entire cassette magazine is therefore preferably cooled.

Commercially usual refrigerators or freezers are used to cool the cassette magazines. The tissue samples can then be retrieved by labeling the refrigerators and/or the individual compartments in the refrigerators, and by corresponding allocation of the individual refrigerators and/or the compartments in the refrigerators to the tissue samples, for example on the basis of a list.

U.S. Pat. No. 6,251,659 B1 discloses a temperature adaptation apparatus. The temperature adaptation apparatus comprises an input chute and an output chute that are arranged at the same height. Multiple cassette magazines are introducible into the apparatus via the input chute. Inside the apparatus, the cassette magazines can be displaced with a laterally arranged slider in the direction toward an output chute. Once the samples in the cassette magazines have reached the desired temperature, they can be removed from the output chute.

SUMMARY OF THE INVENTION

It is an object of the invention to create an apparatus for cooling cassette magazines containing tissue samples that makes possible, in simple fashion, well-organized storage and simultaneous cooling of the cassette magazines containing tissue samples.

This is achieved according to the present invention by an apparatus for cooling cassette magazines containing tissue samples, said apparatus comprising: a housing; a cooling device; and a transport apparatus for transporting one or more cassette magazines within the housing; wherein said housing comprises at least one of an input chute for cassette magazines in the upper region of the housing and an output chute for cassette magazines in the lower region of the housing; and the transport apparatus is adapted to transport the one or more cassette magazines from top to bottom within the housing.

The invention is notable for an apparatus for cooling cassette magazines containing tissue samples, which has a housing, a cooling device, and a transport apparatus for transporting one or more cassette magazines within the housing. This makes possible, in simple fashion, well-organized storage and simultaneous cooling of the cassette magazines, since by way of the transport apparatus the cassette magazine is transportable, in accordance with its cooling state and/or in accordance with the tissue samples in the cassettes, to a predefined location within the apparatus.

In an advantageous embodiment, the transport apparatus is embodied so that the one or more cassette magazines are transportable from top to bottom within the housing. This contributes to particularly advantageous cooling of the cassette magazines, since a natural temperature gradient within the housing can advantageously be utilized. In particular, the cassette magazines can firstly be cooled gently in the upper part of the housing and thus in the warmer part of the housing and, as their intrinsic temperature decreases, can be transported continuously lower down within the housing in order to be further cooled there. This furthermore contributes to energy-saving operation of the cooling device, since the cassette magazines having a higher intrinsic temperature do not unnecessarily heat up the more strongly cooled region in the lower part of the housing.

In a further advantageous embodiment, the transport apparatus encompasses a screw. This contributes to a particularly simple configuration of the transport apparatus. The screw provided is preferably a usual screw such as the one commonly used in screw drives. The screw and the cassette magazines can be embodied so that the screw engages directly onto the cassette magazines themselves. Alternatively thereto, one or more magazine holders can be provided in the housing, by way of which the cassette magazines are then coupled in a manner allowing transportation by the screw. Furthermore, two or more screws can additionally be arranged in the housing.

In this connection, it is particularly advantageous if an axis of the screw is oriented vertically. This contributes to a short transport path for the cassette magazines from top to bottom.

In a further advantageous embodiment, the housing comprises an input chute for cassette magazines in the upper region of the housing. Alternatively or additionally, the apparatus comprises an output chute for cassette magazines in the lower region of the housing. This contributes, in simple fashion, to energy-saving operation of the apparatus, since the temperature fluctuates only insignificantly upon input and output of the cassette magazines, in contrast to the opening and closing of a door of a refrigerator. This further contributes to easy organization of the cassette magazines, since a user of the apparatus cannot arrange the cassette magazines randomly within the housing, but can do so exclusively via the input shaft, and the location of the cassette magazines within the housing of the apparatus is then determined exclusively by the transport apparatus.

In a further advantageous embodiment, the cooling device encompasses one or more Peltier cooling elements on at least one side wall of the housing. This contributes to a particularly simple and effective configuration of the cooling device.

In a further advantageous embodiment, the cooling device encompasses cooling fins in the housing. The cooling fins help the heat occurring in the housing to be discharged quickly via the housing to the environment. This contributes to cooling of the apparatus in particularly simple and energy-saving fashion.

In a further advantageous embodiment, the housing encompasses an air channel that communicates with the remainder of the housing. Communication between the housing and the air channel preferably occurs via one or more cutouts between the housing and the air channel, through which air can flow from the air channel into the housing and back. This can contribute, in simple fashion, to additional or alternative cooling of the housing of the apparatus.

In a further advantageous embodiment, a fan is arranged in the air channel. The fan enables, in simple fashion, air circulation within the air channel and, because of the communication between the air channel and the housing, also within the remainder of the housing. This can further contribute to influencing a temperature gradient within the housing.

In a further advantageous embodiment, the cooling device encompasses an air cooler in the air channel. The air cooler easily makes possible cooling of the air in the air channel, which air is then deliverable by means of the fan, through the air channel, to the remainder of the housing in order to cool the cassette magazines. This, too, can contribute, without particular complexity, to particularly energy-saving cooling of the apparatus.

In a further advantageous embodiment, the cooling device encompasses a base plate of the housing, which plate has at least one cooling element. The base plate having the cooling element enables alternative or additional cooling of the cassette magazines within the housing.

In a further advantageous embodiment, the housing comprises an insulator. The insulator, which in particular is a thermal insulator, contributes to energy-saving operation of the apparatus by preventing the interior of the housing from being heated up by the environment of the housing.

In a further advantageous embodiment, a data reading unit for reading a magazine code of the cassette magazine or magazines is provided in the housing. This contributes particularly effectively to organized storage of the cassette magazines, since it is possible to recognize automatically which cassette magazine is arranged at which point within the housing. The data reading unit is preferably coupled to an external data processing system with which the cassette magazines can be recorded and located.

In a further advantageous embodiment, at least one temperature sensor, with which the temperature of one or more cassette magazines within the housing is ascertainable, is arranged in the housing. This makes it possible to determine, in simple fashion, which of the cassette magazines have already cooled to processing temperature. One or more temperature sensors can be provided for this purpose, preferably at different heights in the housing. Alternatively thereto, a housing temperature model can be created (for example, on a test stand), which model accounts for the temperature gradients within the housing and allows different temperatures within the housing to be ascertained, using the model, with only one temperature sensor.

It is particularly advantageous in this connection if the temperature sensor is also coupled to the external data processing system. It is thereby possible to recognize not only which cassette magazine is present at exactly which location, but also the current temperature of that cassette magazine. This contributes in particularly advantageous fashion to well-organized and simultaneous cooling of the cassette magazines.

BRIEF DESCRIPTION OF THE DRAWINGS

Exemplifying embodiments of the invention are further explained below with reference to schematic drawings, in which.

DETAILED DESCRIPTION OF THE DRAWINGS

Figure 1:
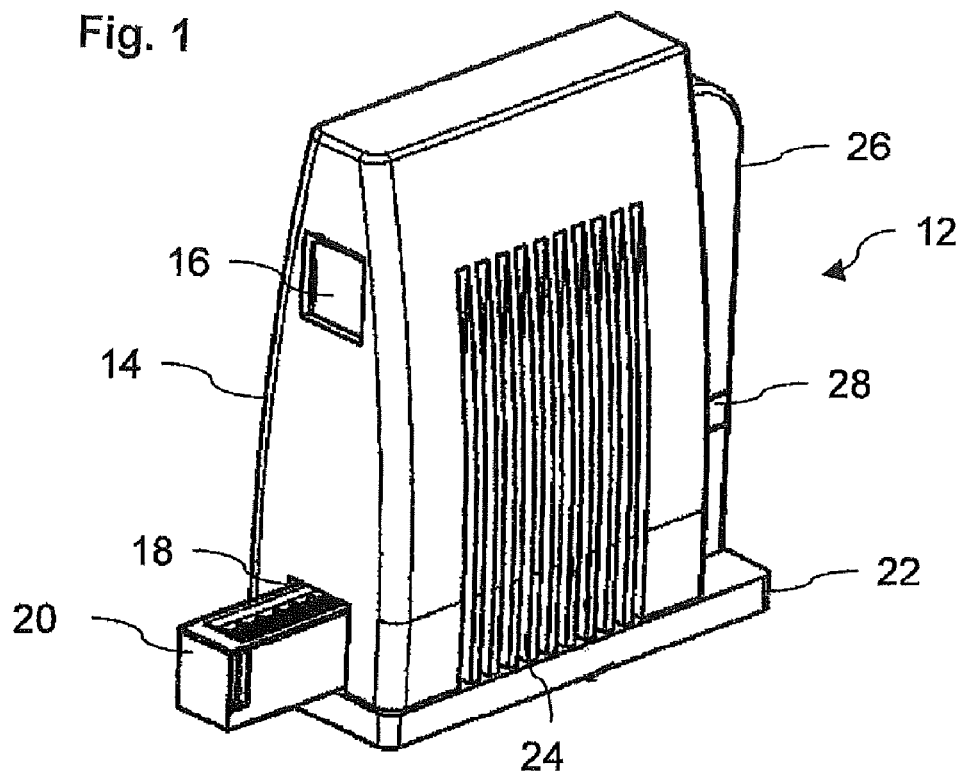
FIG. 1 is a first external view of an apparatus for cooling cassette magazines containing tissue samples.

Elements having the same design or function are identified by the same reference characters throughout the Figures.

FIG. 1 shows an apparatus 12 for cooling cassette magazines 20 containing tissue samples. Apparatus 12 encompasses a housing 14 having an input chute 16 and an output chute 18. Input chute 16 allows cassette magazines 20 to be easily introduced into housing 14. Cassette magazines 20 can be removed again via output chute 18.

Apparatus 12 comprises a transport apparatus with which cassette magazine 20 is transportable from input chute 16 to output chute 18. Cassette magazines 20 are preferably transported from top to bottom in this context. The two chutes 16, 18 and/or the transport apparatus can also be embodied so that multiple cassette magazines 20 are transportable next to one another from top to bottom. Transport from top to bottom advantageously utilizes a natural temperature gradient within housing 14. Cassette magazines 20 are first cooled slowly in the upper, warmer region of housing 14 and then, as their intrinsic temperature drops, are transported farther and farther downward into the cooler region of the housing.

A cooling device of the apparatus can encompass, for example, one or more cooling elements in a base plate 22 of housing 14. Alternatively or additionally, the cooling device can encompass cooling fins 24 of housing 14, by means of which fins the heat occurring in housing 14 can be discharged quickly and easy to the ambient air. Alternatively or additionally, the cooling device comprises an air channel 26 of housing 14, in which channel are arranged, for example, a fan 28 and/or an air cooler.

Figure 2:
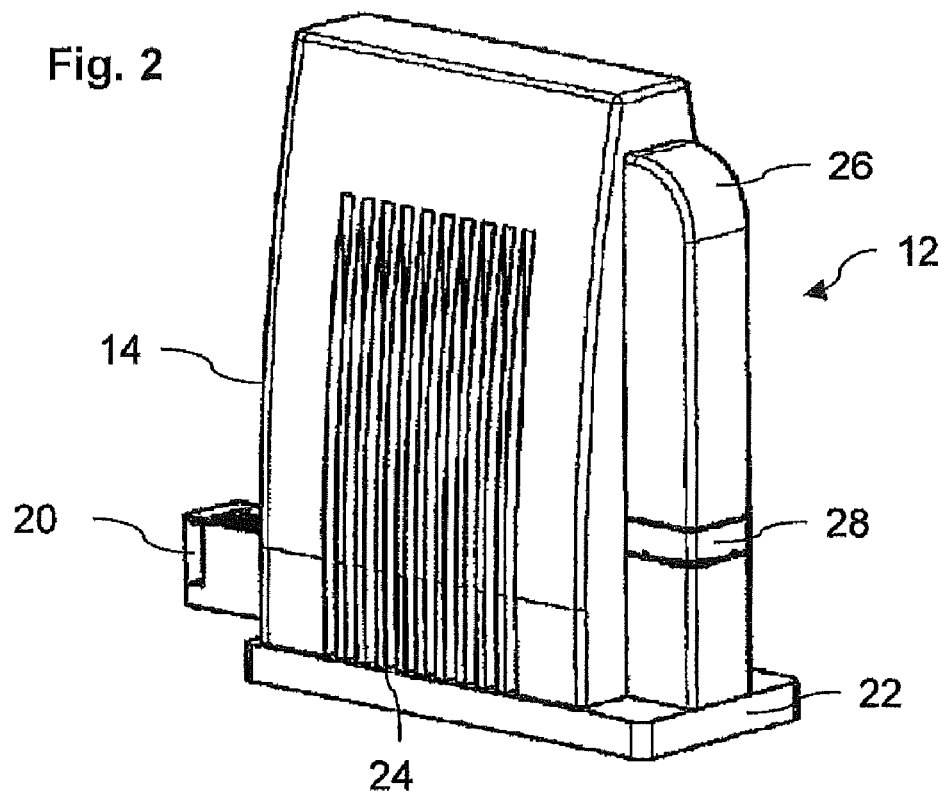
FIG. 2 is a second external view of the apparatus.

FIG. 2 shows apparatus 12 according to FIG. 1 obliquely from behind.

Figure 3:
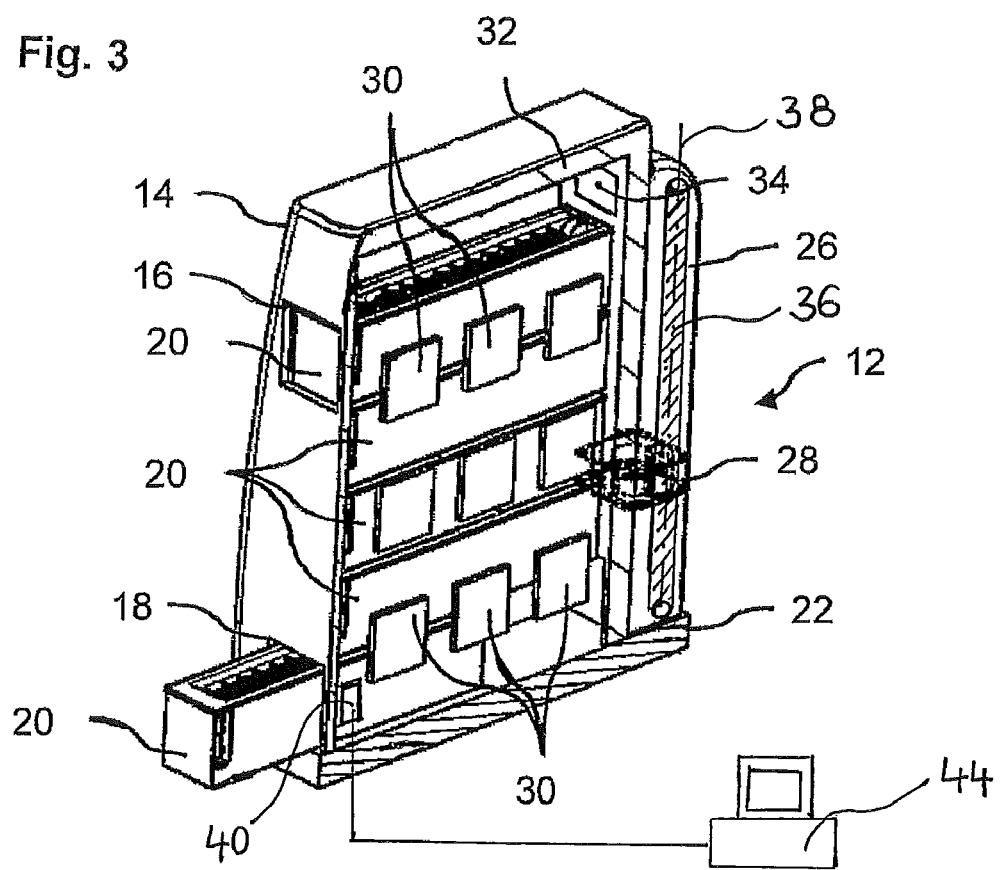
FIG. 3 is a longitudinal section through the apparatus.

A longitudinal section through apparatus 12 in accordance with FIG. 3 shows an opening 34 between air channel 26 and housing 14. At least two openings 34 are preferably embodied between air channel 26 and housing 14, in particular one upstream from fan 28 and one downstream from fan 28. An air flow can be directed through openings 34 out of air channel 26 into housing 14. The air flow can be used to influence the temperature gradients within housing 14. In particular, the air flow can be set so that the temperature gradient in housing 14 is reduced or intensified.

FIG. 3 further shows multiple cassette magazines 20 arranged one above another within housing 14.

The transport apparatus preferably encompasses a screw 36 as known from screw drives, an axis 38 of the screw 36 preferably being oriented vertically. Cassette magazines 20 and the screw 36 can be embodied with respect to one another in such a way that the screw 36 engages directly into cassette magazines 20 themselves. Alternatively thereto, magazine holders can be provided within housing 14, into which holders the cassette magazines 20 are inserted and which are then moved by means of the screw 36. In addition, one or more further screws can be provided in housing 14.

Additionally or alternatively to the cooling elements in base plate 22 and the air cooler in air channel 26, the cooling device can encompass Peltier elements 30 on one or more side walls of housing 14. In addition, housing 14 is preferably equipped with a thermal insulator 32 for better cooling of housing 14.

Figure 4:
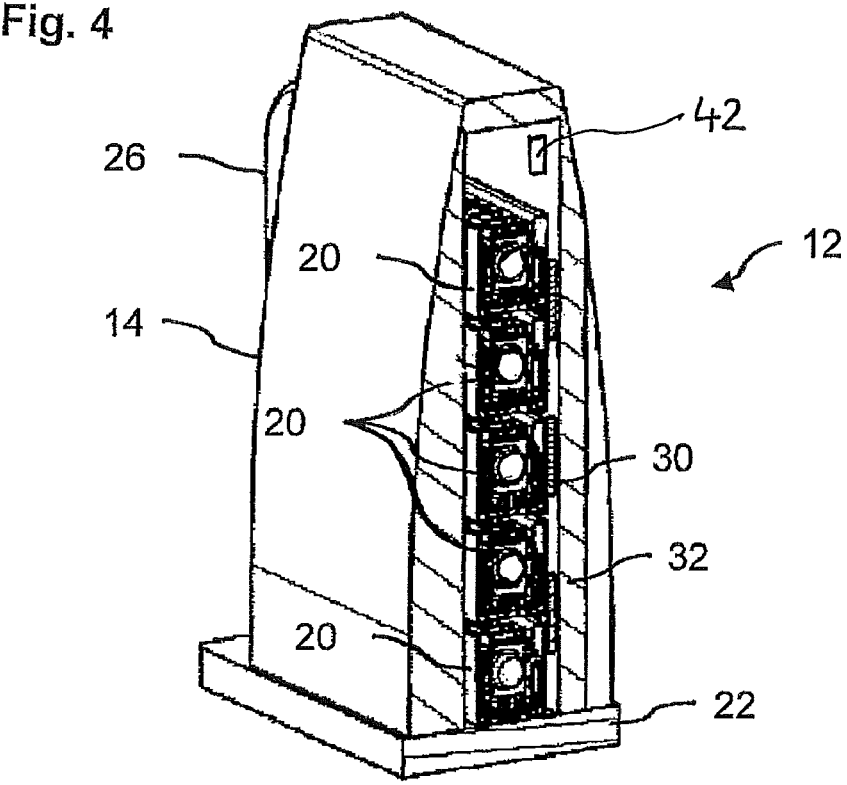
FIG. 4 is a cross section through the apparatus.

The cross section through housing 14 and cassette magazines 20 in FIG. 4 shows, particularly clearly, thermal insulator 32 of housing 14 and the circular tissue samples in cassettes of cassette magazines 20.

A data reading unit 40 and/or a temperature sensor 42 are preferably provided in housing 14. If applicable, both are preferably coupled to an external data processing system 44. The data reading unit 40 enables recognition of a code of the cassette magazines, so that the exact location of the cassette magazines can be read out at the data processing system 44 at any time. The data reading unit 40 encompasses for that purpose, for example, a scanner. In addition, as a function of a temperature signal of the temperature sensor, an intrinsic temperature of cassette magazines 20, and thus of the samples in cassette magazines 20, can be ascertained at any time at the data processing system 44. For this purpose, on the one hand multiple temperature sensors can be provided, in particular at different heights within housing 14. Alternatively thereto, a temperature model for housing 14 can be determined (for example, on a test stand), by means of which model, as a function of a temperature signal of a temperature sensor, the individual intrinsic temperatures of the individual cassette magazines 20 can be determined by way of the temperature gradient within housing 14.

LIST OF REFERENCE NUMERALS

12 Apparatus for cooling tissue samples
14 Housing
16 Input chute
18 Output chute
20 Cassette magazine
22 Base plate
24 Cooling fins
26 Air channel
28 Fan
30 Peltier elements
32 Thermal insulator
34 Opening
36 Screw
38 Axis of the screw
40 Data reading unit
42 Temperature sensor
44 External data processing system

What is claimed is:

1. An apparatus for cooling cassette magazines containing tissue samples, said apparatus comprising:
   a housing with a base plate;
   a cooling device with at least one cooling element in the base plate of the housing;
   an air channel of the housing that communicates with the remainder of the housing and extends from the base plate upwards; and
   a transport apparatus for transporting one or more cassette magazines within the housing; wherein
   said housing comprises an input chute for cassette magazines in the upper region of the housing and an output chute for cassette magazines in the lower region of the housing; and
   the transport apparatus is designed as a transport apparatus that transports the one or more cassette magazines from the upper region within the housing to the lower region so that a temperature gradient of decreasing temperature from the upper region to the lower region is used advantageously for cooling the one or more cassette magazines.

2. The apparatus according to claim 1, wherein the transport apparatus comprises a screw.

3. The apparatus according to claim 2, wherein an axis of the screw extends vertically.

4. The apparatus according to claim 1, wherein the cooling device comprises one or more Peltier cooling elements within the housing on at least one side wall of the housing.

5. The apparatus according to claim 1, wherein the cooling device comprises cooling fins of the housing.

6. The apparatus according to claim 1, wherein the cooling device comprises a fan in the air channel.

7. The apparatus according to claim 1, wherein the cooling device comprises an air cooler in the air channel.

8. The apparatus according to claim 1, wherein the housing comprises an insulator.

9. The apparatus according to claim 1, further comprising a data reading unit that is adapted to read a magazine code of the one or more cassette magazines and is provided in the housing.

10. The apparatus according to claim 1, further comprising at least one temperature sensor arranged in the housing and adapted to determine the temperature of samples in one or more cassette magazines within the housing.

11. The apparatus according to claim 9, wherein the data reading unit is coupled to an external data processing system.

12. The apparatus according to claim 10, wherein the temperature sensor is coupled to an external data processing system.

* * * * *